United States Patent [19]

Wick

[11] 4,205,133
[45] May 27, 1980

[54] APPARATUS FOR FERMENTING LIQUIDS

[75] Inventor: Emil Wick, San Pablo, Calif.

[73] Assignee: The United States of America as represented by the Secretary of Agriculture, Washington, D.C.

[21] Appl. No.: 900,371

[22] Filed: Apr. 26, 1978

[51] Int. Cl.² .............................................. C12M 1/00
[52] U.S. Cl. ..................... 435/287; 99/276; 366/165; 435/813
[58] Field of Search ...................... 195/143, 134, 107; 99/276, 277; 210/532 R, 534, 535; 220/1 R, DIG. 13; 229/20; 366/165, 131, 341, 337; 435/287, 312, 302, 310, 246, 313, 316, 813

[56] References Cited

U.S. PATENT DOCUMENTS

| | | | |
|---|---|---|---|
| 2,083,348 | 6/1937 | Scholler et al. | 195/134 |
| 2,270,616 | 1/1942 | Bell | 210/532 R |
| 3,208,732 | 9/1965 | Ranson | 366/165 |
| 3,528,889 | 9/1970 | Portno | 195/143 |
| 3,880,716 | 4/1975 | Engelbart et al. | 435/313 |

Primary Examiner—S. Leon Bashore
Assistant Examiner—George C. Yeung
Attorney, Agent, or Firm—M. Howard Silverstein; David G. McConnell; Theodore J. Leitereg

[57] ABSTRACT

An apparatus for fermenting liquids is composed of a rear member angularly disposed to the horizontal, two vertical side members attached to the rear member, and a front member angularly disposed to the horizontal attached to the vertical side members and the rear member at its base. The angular disposition between the rear member and the front member is no less than 20° and no more than 140°. The apparatus thus has a small horizontal cross-sectional area at its base and a large horizontal cross-sectional area at its top. An inlet for introducing liquids to be fermented is provided at the base and an outlet for removing fermented liquid is provided at the top of the apparatus. A top member may also be included. The inlet cooperates with the rear member, the two vertical side member, and the front member to create within the fermenting liquid two turbulent zones and a non-turbulent zone. The flow patterns of the liquid within the turbulent zones being opposite and upward for a part of the time, horizontal for a part of the time, and slant for a part of the time.

2 Claims, 6 Drawing Figures

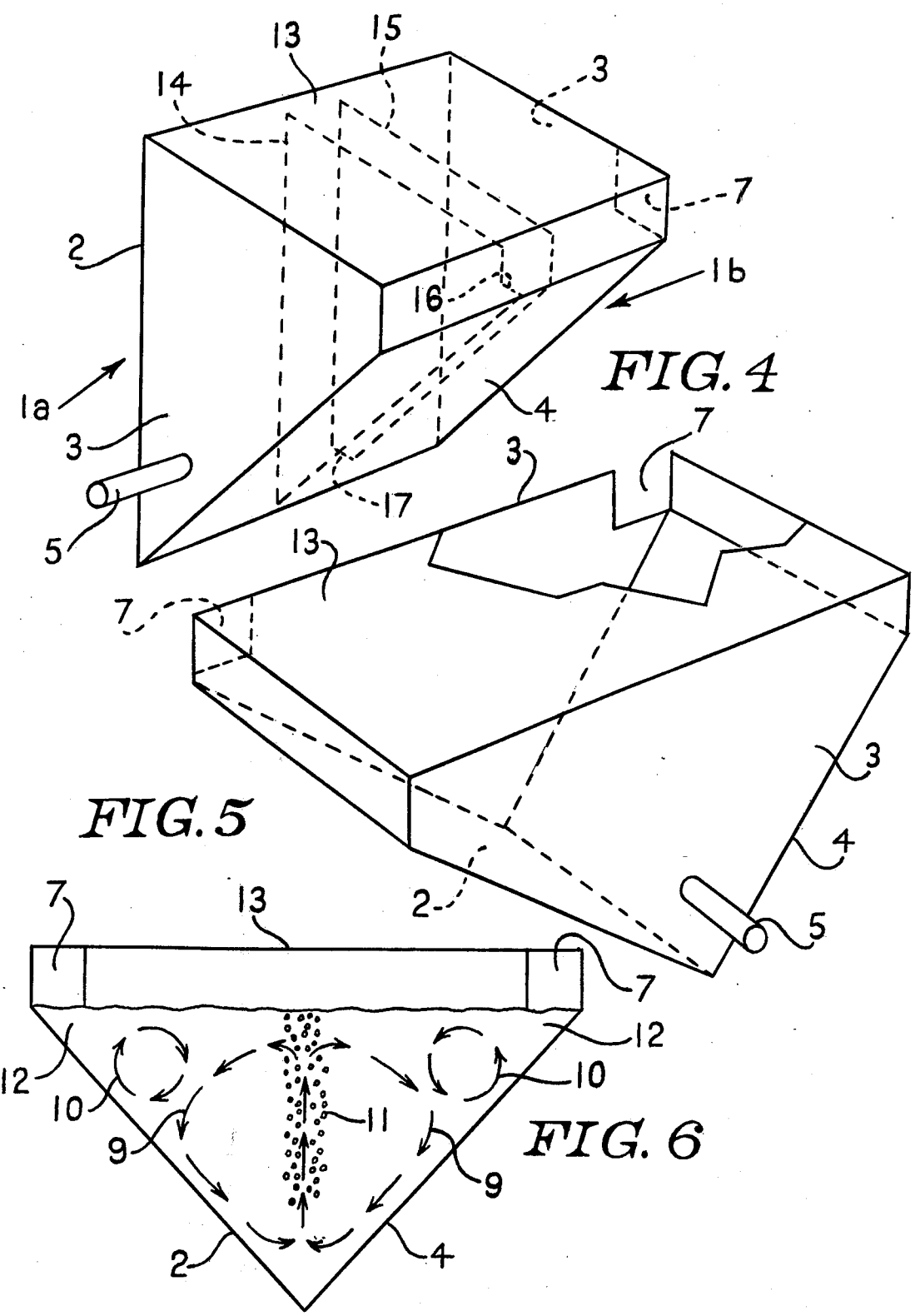

APPARATUS FOR FERMENTING LIQUIDS

BACKGROUND OF THE INVENTION

1. Field of the Invention

This invention relates to and has among its objects the provision of novel methods and apparatus for fermenting liquids. It is a particular object of the present invention to provide means for rapidly fermenting liquids on a continuous flow basis. Further objects of the invention will be evident from the following description wherein parts and percentages are by weight unless otherwise specified.

2. Description of the Prior Art

Fermentation processes are used extensively in the production of beverage products such as beer, wine, whiskey, brandy, and the like. Continuous fermentation of liquids is desirable because of its economic and practical advantages. Batchwise processing results in a considerable amount of settling of the fermentation culture particularly during the latter stages of non-agitated fermentation. In continuous fermentation levitation of the fermentation culture by substrate flow is an important advantage.

Three basic types of continuous flow fermentors are described in Biotechnology and Bioengineering, Vol. XVI, pp. 1611–1631 (1974), by Wick et al. The type of fermentor is determined by the direction of substrate flow: upward flow, slant flow, and horizontal flow. Upward flow is generally obtained in an open cylinder or in a filter fermentor. Slant flow tube and slant flow spiral tube fermentors provide slant flow. Horizontal flow usually results when shallow pans are employed in the fermentation process.

The above described methods have certain inherent disadvantages which render them difficult to use in large scale fermentations. With the upward flow and slant flow methods the tube can be lengthened to accommodate more liquid. However, long tubes become impractical to work with and difficult to conform to the confines of a processing plant. Increasing the diameter of upward flow or slant flow tubes is also disadvantageous for the same reason that horizontal flow is undesirable, namely, settling of the fermentation culture.

SUMMARY OF THE INVENTION

The invention described herein provides means for obviating the problems mentioned above. Liquids are fermented by controlling flow patterns within the liquid so as to retain the fermentation culture medium in a fermenting chamber while at the same time removing fermented liquid free of fermentation culture medium at a rapid rate. Control of the flow patterns within the fermenting liquid is realized by a method wherein liquid to be fermented is applied to a fermenting chamber with a small horizontal cross-sectional are in the influent zone. The chamber is of such design that the horizontal cross-sectional area increases and reaches a maximum in the effluent zone, i.e., the zone at which the fermented liquid is removed from the chamber. The horizontal cross-sectional area in the effluent zone is naturally much larger than in the influent zone. Turbulent zones and a non-turbulent zone are thus created in the fermenting liquid.

The apparatus of the invention has a rear member angularly disposed to the horizontal, two vertical side members attached to the rear member, and a front member angularly disposed to the horizontal attached to the vertical side members and the rear member at its base. The angular disposition between the rear member and the front member is no less than 20° and no more than 140°. A means for introducing liquids to be fermented is provided at the base of the apparatus when the horizontal cross-sectional area is small. Fermented liquid is removed from the apparatus in a non-turbulent zone at a point whereat the horizontal cross-sectional area is large.

The primary advantage of the method and apparatus of the invention is that very rapid fermentations may be accomplished continuously in small fermentors. Consequently, large amounts of final product can be obtained in minimal time and space. The limiting factor determining the time required to complete a fermentation is the rate at which the fermentation culture medium reacts with the substrate. For example, in the production of wine the limiting factor is the rate of reaction between yeast and sugar in the juice. Thus, wine can be prepared in accordance with the invention in a matter of hours whereas conventional fermenting techniques require three to four days.

BRIEF DESCRIPTION OF THE DRAWINGS

FIGS. 4 and 5 are three-dimensional views of other embodiments of the apparatus of the invention.

FIG. 6 is a cross-sectional view of the embodiment illustrated in FIG. 5 depicting the apparatus in operation.

DESCRIPTION OF THE PREFERRED EMBODIMENTS

As mentioned above, the advantages of the invention are realized by controlling flow patterns within the fermenting liquid so that fermentation culture is retained although fermented liquid is removed at a relatively rapid rate. The method of the invention involves continuously passing the liquid to be fermented into a fermenting chamber wherein the horizontal cross-sectional area is small in the influent zone. The horizontal cross-sectional area of the chamber increases gradually and reaches a maximum at a point whereat the fermented liquid is removed, i.e., the effluent zone.

The method of the invention creates three zones within the liquid in the fermenting chamber—two turbulent zones and a non-turbulent zone. The fermentation culture medium is maintained by and within the turbulent zones. The flow pattern within the turbulent zones is upward for a part of the time, horizontal for a part of the time, and slant for a part of the time. The second turbulent zone is considerably smaller than the first and has a flow pattern opposite thereto. Fermented liquid is removed from the fermentor in the non-turbulent zone.

The maximum flow rate of liquid is applied to the fermentation chamber is about one chamber volume every two hours. The rate of flow employed should be no greater or less than that required to produce the above-mentioned flow patterns. It should be obvious that the liquid must be applied to the chamber under a slight pressure to achieve the desired rate; pumping or other suitable technique may be used to obtain this result. The minimum flow rate can be as small as one chamber volume every three to four days or more. However, the primary advantage of the invention is rapid fermentation with times considerably less than conventional techniques, which require, for example, three to four days, at least. It is, therefore, desirable to employ a flow rate near that of the maximum.

The apparatus of the invention is composed of a rear member, two side members, and a front member angularly disposed to the rear member. The apparatus thus has a small horizontal cross-sectional area at its base and a large horizontal cross-sectional area at its top. An inlet is located at the base and an outlet at the top of the present apparatus. A top member may also be included. The rear member may be disposed to the horizontal at an angle of about 90°-160° and the front member at an angle of about 20°-70°. The angular disposition between the rear member and the front member should be no less than 20° and no more than 140°.

Figure 1:
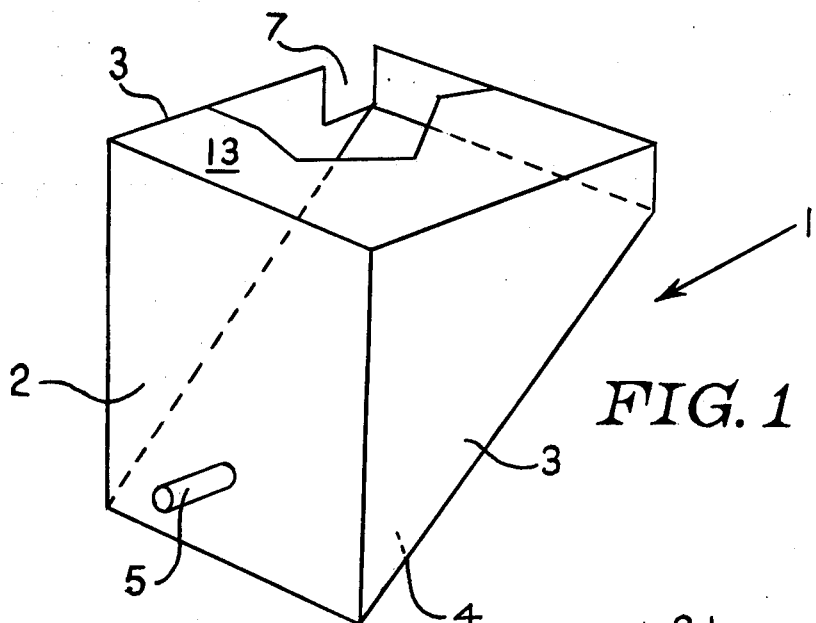
FIGS. 1 and 2 depict in three dimensions a particular embodiment of the apparatus of the invention.
Figure 2:
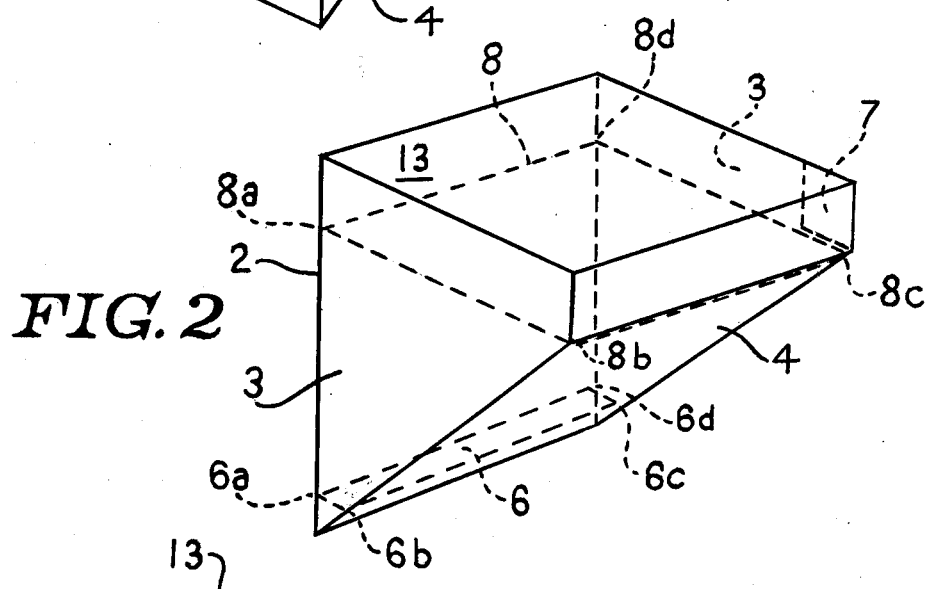

Reference is made to FIGS. 1 and 2 which illustrate a preferred embodiment of the apparatus of the invention. Apparatus 1 takes the form of a partial cube with vertical rear member 2 and vertical side members 3 connected thereto. Angular front member 4 is connected to sides 3 and rear member 2, thus completing the partial cube-like structure. Inlet tube 5 is attached to 2 at its base at a point at which the horizontal cross-sectional area 6 of the fermenting chamber is small. Fermented liquid exits chamber 1 through outlet 7, horizontal cross-sectional are 8 being large and approaching its maximum value at the lowest point of outlet 7. Generally, the ratio of the horizontal cross-sectional areas in the effluent zone and the influent zones is about 4-20 to 1. In the preferred embodiment of the invention depicted in FIGS. 1 and 2 rear member 2 is vertical and front member 4 is disposed to member 2 and the horizontal at angles of 45°. It should be evident that the horizontal cross-sectional area in the effluent zone increases substantially as the angle of disposition of member 4 to member 2 is increased.

Figure 3:
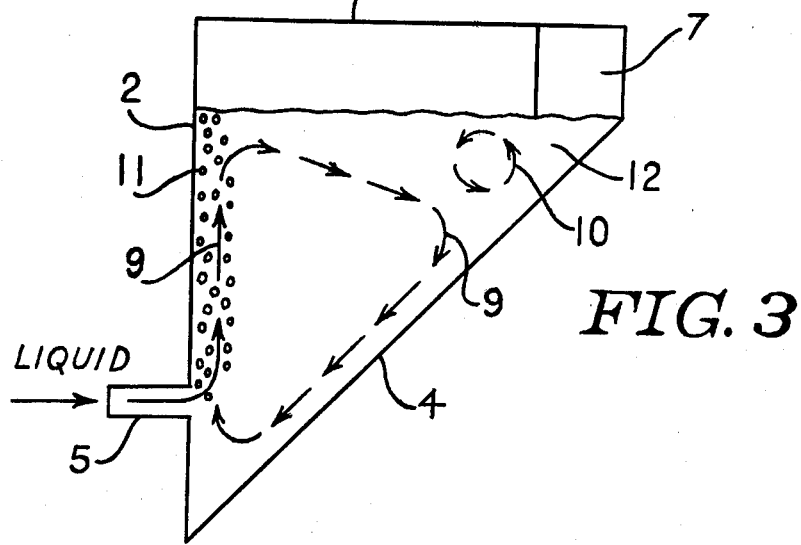
FIG. 3 is a cross-sectional view of the apparatus of FIGS. 1 and 2 depicting the apparatus in operation.

Flow patterns 9 and 10 generated by the method of the invention are depicted in FIG. 3. The liquid to be fermented is pumped through inlet 5 into chamber 1, which contains the fermentation culture medium. As the liquid contacts the culture medium gas bubbles 11 (generally carbon dioxide) are generated due to the metabolization of the substrate by the fermentation culture. These bubbles rise to the top of 1 along rear member 2, the liquid level rising to the bottom of outlet 7. Fermented liquid exits the chamber through outlet 7 and is collected. The fermentation culture medium, however, does not reach the effluent area. Flow patterns or turbulent zones, such as these shown in FIG. 3, are created and the culture medium is maintained within chamber 1. The flow thus created provides intimate mixing of the fermentation culture and the liquid to be treated. Turbulent zones 9 and 10 will be maintained as long as the flow of liquid into chamber 1 is continued. Region 12 is a quiet region or non-turbulent zone with no flow pattern. Thus, fermented liquid simply rises to the bottom of outlet 7 and exits therefrom. Gas 11 accumulates at the top of 1, generally provided with top member 13 to assist in keeping the fermenting liquid free of foreign material. The gas exits 1 through the top region of outlet 7. It should be obvious that 7 must necessarily be positioned somewhere in the non-turbulent zone.

There will be, of course, a point at which the fermentation ceases, because the substrate on which the fermentation culture grows becomes exhausted or because influent is no longer applied to the chamber. The amount of culture medium required can be calculated according to known principles on the basis of the amount of liquid to be fermented and its content of fermentation substrate.

It may be desirable in some fermentations to employ the embodiment of the invention depicted in FIG. 4. Plates 14 and 15 are added to the apparatus of the invention. Plates 14 and 15 conform to the size and shape of chamber 1 with the exception that plate 14 contains opening 16 and does not conform to the height of 1 and plate 15 has opening 17 and also is not as high as chamber 1. Essentially, plates 14 and 15 create two separate fermentation chambers 1a and 1b wherein 16 functions in the same manner as outlet 7 and 17 functions the same as inlet 5. The shorter height of plates 14 and 15 allows gases formed during fermentation to pass freely toward outlet 7. This particular embodiment of the invention may be used to insure complete fermentation in those situations in which less than complete fermentation may occur. It is to be noted that inlet 5 must be positioned, in this particular embodiment of the invention, so that liquid to be fermented enters only chamber 1a.

Another embodiment of the apparatus of the invention is depicted in FIG. 5. Member 2 is no longer vertical. In this particular embodiment member 2 may be disposed to the horizontal at an angle of about 91°-160° and to member 4 at an angle of about 40°-140°. Member 4 may be disposed to the horizontal at an angle of about 20°-70°. The operation of the apparatus of FIG. 5 is depicted in FIG. 6. Flow pattern 9 of the fermentation culture medium occurs upwardly at the center of the apparatus then horizontally across below the top of the apparatus and finally along members 2 and 4. Gas bubbles rise to the top of the apparatus and exit through outlet 7. Fermented liquid leaves the apparatus through the bottom of outlets 7, positioned in non-turbulent zones 12.

The invention is of wide versatility and may be used in all type of fermentations of liquids including yeast-alcohol fermentations, e.g., wine, beer, chemical alcohol, etc., other microbial fermentations, e.g., lactic acid fermentation, etc., and the like. As various changes could be made in the aforementioned method and apparatus without departing from the scope thereof, it is intended that all matter contained in the above description shall be interpreted as illustrative and not in a limiting sense.

The apparatus of the invention can be fabricated from all types of materials, such as wood, concrete, plastic, and the like.

Having thus described my invention, I claim:

1. An apparatus for fermenting liquids, which comprises a rear member disposed to the horizontal at an angle of about 90°-160°, two vertical side members attached to said rear member, a front member attached to said vertical side members and said rear member at its base, said front member being disposed to the horizontal at an angle of about 20°-70°, the angular disposition between said rear member and said front member being no less than 20° and no more than 140°, the apparatus thus having a horizontal cross-sectional area at its base substantially less than the horizontal cross-sectional area at its top, means for introducing liquids to be fermented into the apparatus attached to the base of the apparatus, said means cooperating with said rear member, said vertical side members, and said front member to create within the fermenting liquid two turbulent zones and a non-turbulent zone, the flow patterns of the liquid within the turbulent zones being opposite and upward for a part of the time, horizontal for a part of the time, and slant for a part of the time, and means for removing fermented liquid from the apparatus at the top of the apparatus.

2. The apparatus of claim 1 which further comprises a top member attached to said rear member, said vertical side members, and said front member.